United States Patent [19]

Anderson et al.

[11] Patent Number: 5,681,706
[45] Date of Patent: Oct. 28, 1997

[54] MAMMALIAN ANOXIA-RESPONSIVE REGULATORY ELEMENT

[75] Inventors: Garth R. Anderson, Elma, N.Y.; Scott D. Estes, Somerville, Mass.; Daniel L. Stoler, Getzville, N.Y.

[73] Assignee: Health Research Inc., Buffalo, N.Y.

[21] Appl. No.: 609,657

[22] Filed: Mar. 1, 1996

[51] Int. Cl.$^6$ .................................................. C12Q 1/68
[52] U.S. Cl. .................. 435/6; 435/91.1; 435/172.3; 435/69.1; 435/353; 435/375; 435/320.1; 536/24.1
[58] Field of Search .................. 435/320.1, 240.2, 435/252.33, 91.1, 172.3, 69.1, 6, 353, 375; 536/24.1

[56] References Cited

PUBLICATIONS

Anoxic Induction of a Sarcoma Virus–Related VL30 Retrotransposon is Mediated by a cis–acting Element Which Binds Hypoxia–Inducible Factor 1 and an Anoxia–Inducible Factor, Scott D. Estes et al., Journal of Virology, Oct. 1995, vol. 69, No. 10, pp. 6335–6341.

Firulli et al., *J. Virol.*, vol. 67, 1993, pp. 6857–6862.

Wang et al., *PNAS*, vol. 90 1993, pp. 4304–4308.

*Primary Examiner*—James Ketter
*Attorney, Agent, or Firm*—Hodgson, Russ, Andrews, Woods & Goodyear

[57] ABSTRACT

Genetic regulatory elements which effect anoxic induction of a DNA molecule in mammalian cells exposed to anoxia are identified. The genetic regulatory elements, designated mammalian anoxia-responsive elements, when operably linked to a DNA molecule and basal promoter regulate the transcription of the DNA molecule in response to anoxia. The invention relates to recombinant vectors useful for introduction into mammalian cells, and the selective expression in mammalian cells exposed to anoxic conditions. Also provided are methods of using such vectors.

16 Claims, 2 Drawing Sheets

Induction by Anoxia

MAMMALIAN ANOXIA-RESPONSIVE REGULATORY ELEMENT

This invention was made with government support under grant numbers RO1-CA48828, and DAMD-1791-C1003 awarded by the National Institutes of Health and the Department of Defense, respectively. The government has certain rights in this invention.

FIELD OF THE INVENTION

The present invention relates to mammalian gene expression under conditions of reduced oxygen tension. More particularly, the invention relates to a genetic element which regulates gene expression in response to anoxia. Nucleic acid constructs containing nucleic acid sequences, encoding a desired gene product and operably linked to this anoxia-responsive regulatory element will enable the selective expression to the desired gene product under anoxic conditions in mammalian cells.

BACKGROUND OF THE INVENTION

Under most natural physiological conditions encountered by a mammalian cell, there are few instances where a cell is exposed for a prolonged period of time to anoxic conditions or anaerobiosis. However, there are some normal physiological conditions, and some pathological conditions, in which cells are exposed to anoxia. The cell response to anoxia is characterized by the ability to alter gene expression in coping with such conditions of reduced oxygen tension.

1. Physiological condition

A cell response to anoxia is physiologically expressed in wound healing. Wound healing is a multistep, multicellular process that involves shifting oxygen levels in the wound environment. The initial step of wound healing is characterized by clotting, fibrin formation, and neutrophil infiltration. Neutrophil infiltration provides phagocytic and lysosomal activity. A second step involves macrophage and fibroblast infiltration into the wound thereby facilitating debridement and inflammation.

In this second step, enzymes are secreted which digest cellular debris and breakdown intercellular matrices which anchor such cellular debris. Thus, through both phagocytosis and the activity of secreted enzymes, large scale removal of wound debris is effected. Anoxic conditions prevail in the interior of the wound until the completion of angiogenesis; i.e., approximately one week after wounding. Subsequent steps involve fibroblast proliferation; extensive collagen production; capillary formation; and finally myofibroblast contraction leading to compression, disappearance of capillaries, and scar tissue formation.

The cellular response to anoxia encountered in wound healing has been well studied. For example, the low oxygen tension in the wound induces macrophages to secrete TNFα which promotes angiogenesis. During anoxia, fibroblasts are metabolically active, with energy coming from glycolysis. Two metalloproteinases, cathepsins D and L, are secreted thereby contributing to debridement (Stoler et al., 1992, *Cancer Res.* 52:4372–4378; Anderson et al., 1995, *J. Surg. Res.* 59:666–674). Other secreted enzymes include endonucleases (Russo et al., 1995, *Cancer Res.* 55:1122–1128) which functions to degrade chromatin released from damaged cells; and a protein having κ-isozyme lactate dehydrogenase (LDH-κ) activity (Anderson et al., 1995, supra). Anoxia also induces fibroblasts to exhibit a delayed (7 or more days later) contractile response that leads to scar tissue formation (Anderson et al. 1995, supra).

2. Pathological condition

Solid tumors frequently contain regions of near anoxia (Nicolson, 1987, *Cancer Res.* 47:1473–1487). Nascent tumors prior to neovascularization also contain regions of near anoxia (Brown et al., 1994, *Intl. J. Radiat. Biol.* 65:95–102). An anoxia-inducible endonuclease is constitutively expressed in human colorectal tumors but not in normal colorectal tissue samples (Russo et al., 1995, supra). This endonuclease, endonuclease-NX is also the major endonuclease produce by anoxic fibroblasts in wound healing as shown by biochemistry, isoelectric focusing, and by molecular mass (Mr 29,000/31,000 doublet). Parallel with the expression of endonuclease-NX in anoxic fibroblasts and in malignant tumor appears genomic instability. Genomic stability is a major factor in the evolution of normal cells into malignancy, and of malignancy to metastases (Cheng et al., 1993, *Adv. Cancer Res.* 60:121–156). While other mechanisms may contribute to genomic instability in tumorigenesis, DNA breakage resulting from endogenous endonuclease activity can have a substantial effect in modulating genomic instability.

3. VL30 Elements

To study the anoxic fibroblast response, normal rat fibroblasts are cultured in 5% $CO_2$ in an anaerobic chamber. The earliest known event is the transcriptional activation of VL30 retrotransposon sequences. Induction of SVL30 RNA expression is common to the anoxic fibroblast response and to malignant tumor cells. VL30 sequences are a multigene family with multiple copies in the rat and mouse genomes. These are endogenous sequences placed in the retrotransposon class of mobile genetic elements since they are packaged by retroviruses and integrated into new sites in the chromosome. VL30 sequences are often highly transcribed in murine cancers. SVL30 sequences, sarcoma virus-related VL30 retrotransposon sequences, are a class of VL30 sequences. Anoxic stimulation of normal rat fibroblasts is capable of inducing SVL30 RNA by 50–300 fold (Anderson and Stoler, 1993, *BioEssays* 15:265–271). In addition to being present in cellular DNAs from mice and rats, nucleotide sequences homologous to VL30 DNA were detected in human cells (Itin et al., 1983, *Virology* 127:374–384).

Some inducible elements contained in VL30 sequences have been characterized. The long terminal repeat of a VL30 retrotransposon was found to contain two retinoic acid-responsive elements (RREs) required for retinoic acid induced transcription in cultured mouse keratinocytes and normal human keratinocytes (Islam et al., 1993, *J. Biol. Chem.* 268:3251–3259). Similarly, the long terminal repeat of a VL30 retrotransposon was found to contain a 12-O-tetradecanoylphorbol-13-acetate (TPA)-responsive element required for TPA-induced transcription in cultured mouse keratinocytes and normal human keratinocytes (Bohm, 1991, *J. Biol. Chem.* 266:24834–24841). Taken together, the mechanisms of various regulatory elements associated with VL30 sequences are conserved in evolution between mammalian species.

To date, there have been no reports of practical means to regulate gene expression in anoxic conditions. The identification of a mammalian element responsive to anoxia, an anoxia-responsive element, would enable one to regulate the expression of genes involved in such processes as wound healing, retinopathy (Craitoiu, 1992, *Oftalmologia*, 36:141-8), and malignancy. Alternatively, in a nucleic acid construct containing a promoter, an anoxia-responsive element, and a desired gene operably linked thereto, such a gene which may not normally be expressed in anoxic conditions can then be so expressed.

SUMMARY OF THE INVENTION

The present invention provides the first identified isolated mammalian transcriptional regulatory element that is a cis-acting element capable of functionally discriminating between anoxia versus hypoxia. Thus, a primary object of this invention is to provide a method which enables those skilled in the art to selectively express a DNA molecule under anoxic conditions.

Another object of the present is to provide a means by which a DNA molecule not normally expressed in anoxia is operably linked to a promoter and a mammalian anoxia-responsive element thereby enhancing the expression of the DNA molecule under anoxic conditions.

Another object of the present invention is to provide a recombinant DNA molecule or recombinant vector comprising a mammalian anoxia-responsive element, a promoter capable of expression in mammalian cells, and a DNA molecule to be expressed; wherein the DNA molecule is located 3' to, and operably linked with, the promoter; wherein the promoter-DNA molecule combination is operably linked with the mammalian anoxia-responsive element so that the mammalian anoxia-responsive element induces transcription of the promoter-DNA molecule combination under anoxic conditions and in a mammalian cell.

Another object of the invention includes a cell which contains a vector comprising a mammalian anoxia-responsive element and a mammalian-expressible promoter, and a DNA molecule to be expressed under anoxic conditions.

Another object of the invention is to provide a method for regulating the expression of a DNA molecule under anoxic conditions which comprises:
(a) operably linking the DNA molecule to a mammalian-expressible promoter and a mammalian anoxia-responsive element in a vector in forming a recombinant vector;
(b) introducing the recombinant vector into a host mammalian cell expression compatible with the mammalian-expressible promoter and mammalian anoxia-responsive element; and
(c) (i) wherein the host cell encounters anoxia in a natural environment (in vivo), or
(c) (ii) culturing the host cell (in vitro) and regulating the expression of the desired DNA molecule by reducing the oxygen tension of the culture medium to anoxic conditions.

A further object of the present invention is to provide methods of using host cells containing a recombinant vector comprising a DNA molecule operably linked to a mammalian-expressible promoter and a mammalian anoxia-responsive element in a vector construct.

An additional object of the present invention is to provide a method for making, including identifying and mapping, other mammalian anoxia-responsive elements from cellular or viral-like DNA which are the functional equivalent of the mammalian anoxia-responsive element (SEQ ID NO:1) disclosed in the present invention in facilitating the expression of a DNA molecule under anoxic conditions.

DESCRIPTION OF THE INVENTION

Definitions

By the terms "anoxia", "anoxic conditions" and "near anoxia" are meant, for the purposes of the specification or claims, an environment of reduced oxygen tension such that the oxygen content is in the range of less than 0.1% to 0% (complete anaerobiosis).

By the term "hypoxia" is meant, for the purposes of the specification or claims, an environment of reduced oxygen tension such that the oxygen content is in the range of 0.1% to 1.0%.

By the terms "mammalian anoxia-responsive element" and its "functional equivalent" is meant, for the purposes of the specification or claims, a genetic element present in cellular or viral-like DNA which
(a) when placed in a cis-acting orientation and operably linked to a mammalian-expressible promoter and a desired DNA molecule regulates the expression of a DNA molecule under anoxic conditions in a mammalian cell;
(b) in response to anoxic conditions, enhances transcription of an operably-linked promoter-DNA molecule combination;
(c) is capable of discriminating between hypoxia and anoxia, i.e., is responsive only to anoxic conditions; and
(d) is made according to the methods of the present invention for making a mammalian anoxia-responsive element.

Figure 3:
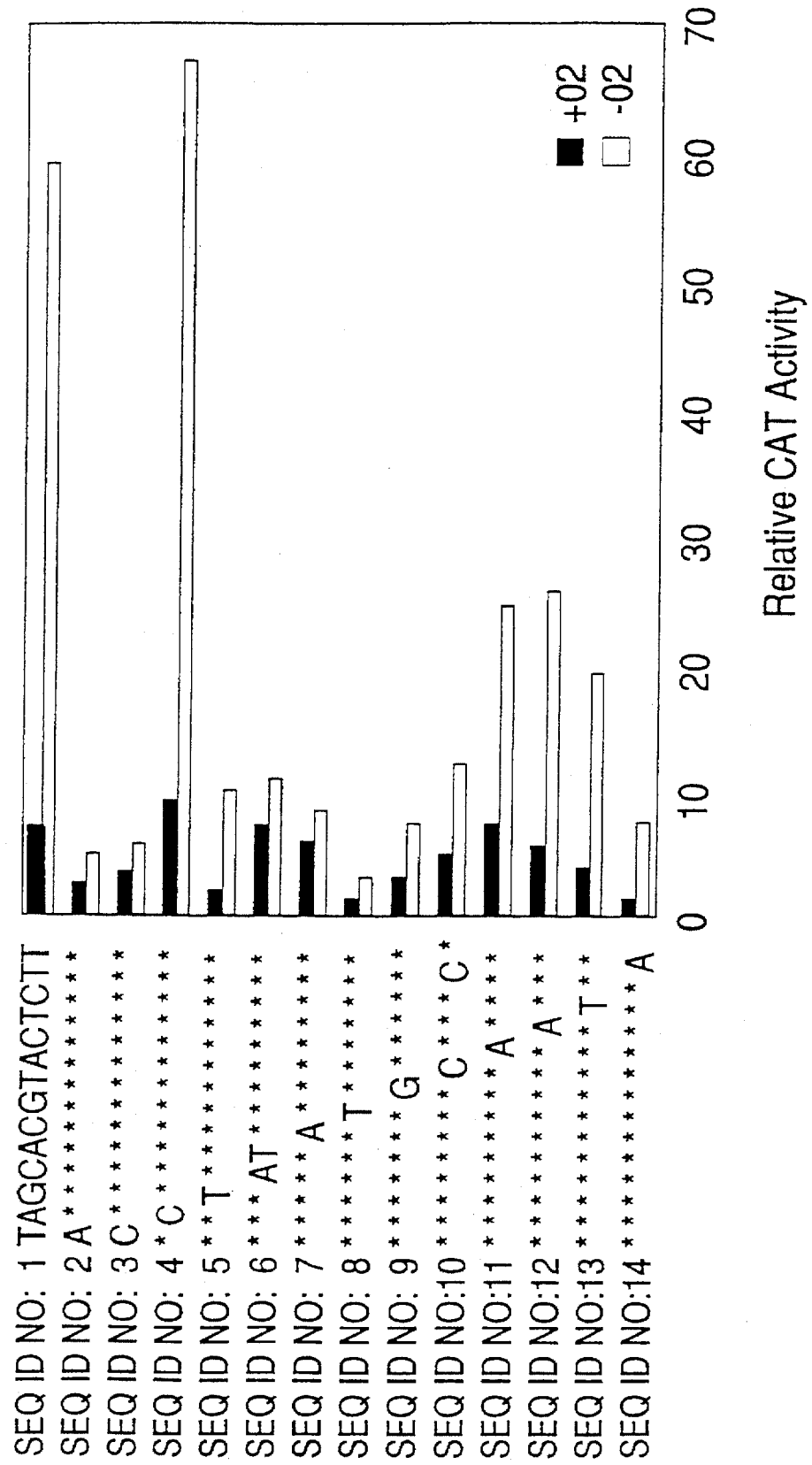
FIG. 3 is a schematic representation showing the effect of various point mutations on the anoxic inducibility of SEQ ID NO:1; wherein anoxic inducibility is represented by CAT activity ($-O_2$) compared to CAT activity in aerobic culture ($+O_2$).

Additionally, as shown in FIG. 3, for example, a DNA sequence which is identical in nucleotide sequence to the mammalian anoxia-responsive element disclosed in SEQ ID NO:1, except for a base change or substitution, may function substantially (ranging from approximately 50% of the activity to greater than 100% of the activity of SEQ ID NO:1) as SEQ ID NO:1, and thus is a functional equivalent because of the ability to substantially induce the expression of a desired DNA molecule in the cells under anoxic conditions.

By the term "operably linked" is meant, for the purposes of the specification and claims to refer to the chemical fusion (restriction with subsequent ligation) or synthesis of DNA such that a mammalian anoxia-responsive element-promoter-DNA molecule combination is formed in a proper orientation and reading frame for the DNA molecule to be transcribed into functional RNA with the transcription being regulated by the mammalian anoxia-responsive element and promoter. In the construction of the mammalian anoxia-responsive element-promoter-DNA molecule combination, it is generally preferred to position the promoter at a distance upstream from the initial codon of the DNA molecule that is approximately the same as the distance between the promoter and the gene it controls in its natural setting. However, as known in the art, some variation in the distance can be accommodated without loss of promoter function. Likewise, it is generally preferred to position the mammalian anoxia-responsive element either at a distance upstream from the promoter, incorporated into the promoter sequences as a promoter element, located between the promoter and the DNA molecule to be expressed, or located within the first third of the coding region of the DNA molecule to be expressed, in a manner approximately the same as between the mammalian anoxia-responsive element and the promoters it controls in its natural setting. However, as known in the art, some variation in the placement can be accommodated without loss of the genetic element's function.

By the terms "consisting essentially of a nucleotide sequence" is meant, for the purposes of the specification or claims, the nucleotide sequence disclosed, and also encompasses nucleotide sequences which are identical except for a one base change or substitution therein.

By the term "Individual" is meant, for the purposes of the specification and claims to refer to any mammal, especially humans.

By the term "DNA molecule" is meant, for the purposes of the specification and claims to refer to a nucleic acid sequence selected from the group consisting of a gene which encodes a desired gene product comprising a protein, more than one gene, a gene fragment comprising a portion of a gene which encodes a desired peptide, and antisense (a strand of DNA complementary) to a gene. The expressed proteins or peptides may include biologically-active, and/or commercially valuable molecules known to those skilled in the art.

By the term "mammalian cell capable of undergoing an anoxic response" is meant, for the purposes of the specification and claims to refer to fibroblasts, endothelial cells, keratinocytes, hepatocytes, monocytes, macrophages, myogenic cells, retinal cells, tumor cells, and cell lines of each of the foregoing cell types.

By the terms "mammalian-expressible promoter" or "promoter" is meant, for the purposes of the specification and claims to refer to a nucleotide sequence involved in binding of RNA polymerase to initiate transcription of a DNA molecule operably linked to the sequence; wherein such binding function of the sequence occurs in mammalian cells. Such promoters are known to those skilled in the art and may include viral or viral-like basal promoters like the SV40 late promoter, the RSV promoter, the CMV immediate early promoter, and a VL30 promoter; and cellular promoters (See, e.g., Larsen et al., 1995, *Nucleic Acids Res.* 23:1223–1230; Donis et al., 1993, *BioTechniques* 15:786–787; Donda et al., 1993, *Mol. Cell. Endocrinol.* 90:R23–26; and Huper et al., 1992, *In Vitro Cell Dev. Biol.* 28A:730–734).

The ability of anoxia to impact both normal physiological processes and pathological processes depends largely upon modulation of gene expression in cells exposed to anoxic conditions. To investigate the modulation of gene expression by anoxia, an in vitro model system has been developed which correlates with the changes in gene expression observed for in vivo processes during anoxia (See, e.g., Stoler et al., 1992, *Cancer Res.* 52:4372–4378). This model is comprised of normal rat fibroblasts (e.g., Fischer rat embryo cell line, "FRE") which are cultured anoxically. Under such culture conditions, full viability of the fibroblasts remains for at least the first two full days of anoxia, and viability has been noted to continue after 72 hours of anoxia (Stoler et al., supra). The cell viability is not unexpected as fibroblasts must function metabolically without oxygen in certain steps of wound healing where the wound site is essentially anoxic.

The initial response to anoxia by the normal rat fibroblasts is the induction of transcription of SVL30 sequences within approximately an hour after onset of anoxia. Several hours after onset of anoxia, cellular DNA synthesis stops; and adaptation to glycolytic metabolism occurs resulting in elevation of hexose transport, induction of glycolytic enzymes including LDH-κ. SVL30 sequences, occurring throughout the genome, are thought to be truncated endogenous members of the complex retrovirus family.

It has been shown that the induction observed for SVL30 RNA levels in anoxic normal rat fibroblasts is similar to the levels of SVL30 RNA observed in rat tumor cell lines cultured aerobically (Anderson and Stoler, 1993, supra). However, at the time of the invention, it was unclear why SVL30 sequences are induced in the anoxic fibroblast response, and in malignant tumors; and whether or not their induction had any significance to these processes. Additionally, anoxia induces in both wound healing and malignancy enhanced production and secretion of metalloproteinases cathepsins D and L, endonuclease-NX, and LDH-κ. At the time of the invention, the specific mechanism for anoxic induction of these proteases was not characterized.

In analyzing anoxia-inducible SVL30 RNA from the anoxic FRE fibroblasts, a genetic element was discovered. Isolation and characterization of this genetic element revealed that it is a 14 base pair (bp) cis-acting anoxia-specific element which, when induced, enhances transcription of a promoter-DNA molecule combination in an anoxic mammalian cell. This element has been termed a "mammalian anoxia-responsive element".

A more complete appreciation of the invention, and its many attendant advantages thereof, may become apparent by referring to the following Examples which are provided to aid in the understanding of the features of the invention, and to enable one skilled in the art to make and use the novel mammalian anoxia-responsive element of the invention. The following Examples are intended to be illustrative of the invention, and are not to be construed as limiting the scope of the invention.

EXAMPLE 1

Methods for making a mammalian anoxia-responsive element

Using the illustrative methods and constructs according to the present invention, a mammalian anoxia-responsive element from cellular or retroviral DNA may be identified, mapped, and thereby produced. It is apparent to those skilled in the art that cellular and retroviral DNA may contain mammalian anoxia-responsive elements that are the functional equivalent of the mammalian anoxia-responsive element represented in SEQ ID NO:1 of the present invention. That is, a mammalian anoxia-responsive element may be present in cellular DNA or retroviral DNA; and become active in response to induction by anoxia, thereby regulating transcription and facilitating expression from a desired DNA molecule such as a gene into a respective gene product. To illustrate this embodiment, it is apparent that since the presence of VL30 sequences is conserved in evolution between mammalian species, functional equivalents of the mammalian anoxia-responsive element (SEQ ID NO:1) exist. VL30 sequences may be selected, based on such parameters as homology to SEQ ID NO:1, or frequency of occurrence of particular sequences in cell types showing changes in gene expression in response to anoxia. Alternatively, a cDNA library made from VL30 containing message expressed in anoxic cells can be screened for anoxia responsiveness.

In one illustration of this embodiment, a cDNA library was constructed using RNA, isolated from cultured FRE cells which had been exposed to 6 hours of anoxia (Estes et al., 1995, *J. Virol.* 69:6335–6341) in a lambda GT11 expression vector in accordance with the manufacturer's recommendations. Approximately $10^6$ plaques were screened by hybridization on nitro-cellulose filters to a VL30-specific probe (Firulli et al., 1993, *J. Virol.* 67:6857–6862). A refined version of this probe is disclosed as SEQ ID NO:15. To isolate the clones containing long terminal repeats (LTRs), DNA from the plaques positive in hybridization was amplified by enzymatic amplification using a primer specific for lambda GT11 vector sequences, and a primer specific for VL30 sequences (SEQ ID NO:16). Clones which generated an amplified nucleic acid molecule of the size expected to contain an intact 3' U3 portion of the LTR (approximately 1.2 kb) were subcloned into a reporter vector to be screened for anoxic responsiveness. This strategy was chosen because the genomic structure of these VL30s is similar to that of retroviruses, in that the U3 portion of the 3' LTR can be found intact at the 3' end of anoxia-induced VL30 mRNA. Using this strategy, the clones screened yielded several U3-bearing VL30 clones.

A reporter construct is used for screening a nucleic acid molecule, such as a U3-bearing VL30 sequence, for anoxia responsiveness. A suitable reporter construct is pKT, a pUC18-based plasmid containing a promoterless chloramphenicol acetyltransferase (CAT) gene. The nucleic acid molecule to be screened is inserted into a cloning site of pKT (e.g. SmaI site). The recombinant reporter vector is then used for transfections of FRE cells. Subconfluent FRE cells were transiently transfected with the recombinant reporter vector (12 μg of DNA per 10 cm-diameter culture dish) by the calcium phosphate method. Twelve hours after transfection, cells were released by trypsinization, and divided equally among plates. Transfected cells were placed in a humidified anaerobic glove box and supplied with an 85% $N_2$-10% $H_2$-5% $CO_2$ gas mixture for various periods ranging from 2 hours to 20 hours of anoxia. Cells were then harvested and assayed for CAT activity as described previously (Gorman et al., 1982, *Mol. Cell. Biol.* 2:1044–1051).

Figure 1:
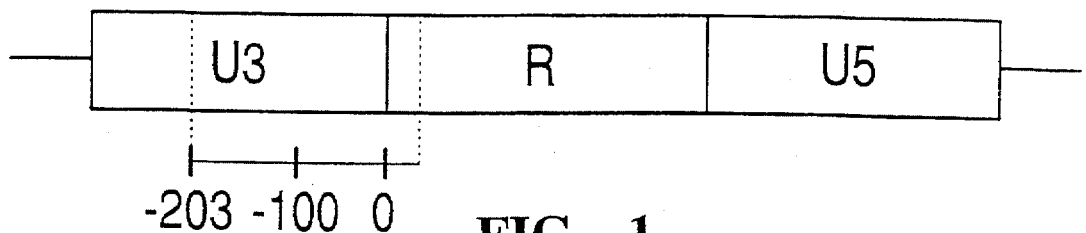
FIG. 1 is a schematic representation showing the location of clone p-203/25, containing a mammalian-anoxia responsive element, in relation to the regions which make up the VL30 long terminal repeat (LTR).

One clone, termed p-203/25, comprising mostly of U3 sequences and terminating just 5' of the polyadenylation signal in the R region (FIG. 1), conferred anoxia inducibility of CAT activity beginning after 8 hours of anoxia to a level approximately 6 times that of the aerobic control. At the RNA level, using Northern blot analysis, under anoxia p-203/25 conferred a 28-fold induction of transcription to CAT mRNA. The mammalian anoxia-responsive element contained within a nucleic acid molecule can be identified further by deletion mapping experiments using methods similar to the following.

Figure 2:
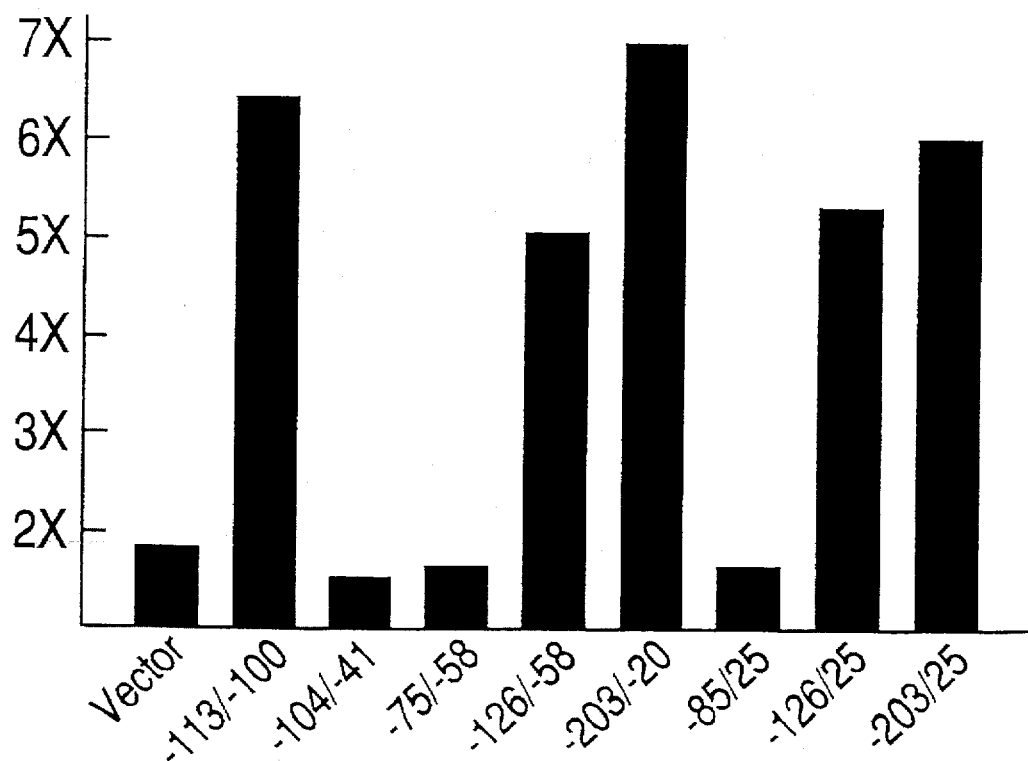
FIG. 2 is a schematic representation showing the anoxic inducibility of each deletion construct made from p-203/25. Anoxic inducibility is represented by CAT activity, expressed as induction relative to that of the aerobic control.

A series of deletion constructs of p-203/25 were generated to precisely define the particular nucleotide sequence within p-203/25 that is anoxia-responsive. Each deletion construct contained a portion of the p-203/25 sequence inserted into a CAT reporter vector, wherein the sequence was inserted downstream from a basal SV40 promoter but upstream from the CAT gene. 5' deletions were created by digestion of p-203/25 at a restriction enzyme site 5' to the inserted sequence, followed by Bal31 digestion of the 5' end and subsequent ligation in the CAT reporter vector. Two 5' deletion constructs were created (p-126/25 and p-85/25; FIG. 2). Several 3' deletion constructs were created by enzymatically amplifying by polymerase chain reaction specific portions of p-203/25, and cloning the amplified fragments into a CAT reporter vector (p-203/-20, p-126/-58, p-126/25, p-113/-100, p-75/-58; FIG. 2; Estes et al., 1995, supra). FRE cells were transiently transfected with respective 5' deletion constructs, 3' deletion constructs, p-203/25, or reporter vector alone. The transfected cells were then divided equally between two dishes; i.e., one to be induced by anoxia, and one as an aerobic control. After 5 hours of growth, cells to be anoxically induced were placed in an anoxic atmosphere (e.g. 85%$N_2$-10%$H_2$-5%$CO_2$) for 20 hours before harvesting and assaying for CAT activity. The CAT activity (expressed as induction relative to that of the aerobic control) representing the anoxic inducibility in each construct is illustrated in FIG. 2. As shown in FIG. 2, anoxia inducibility of gene expression is localized to a 14 bp sequence, as represented by p-113/-100, consisting essentially of the nucleotide sequence of SEQ ID NO:1. Thus, this 14 bp sequence is a mammalian anoxia-responsive element, which can then be isolated from the deletion construct using methods known in the art such as restriction enzyme digestion and subsequent purification. Having produced an isolated and purified mammalian anoxia-responsive element, further large scale isolation and production of a mammalian anoxia-responsive element of a particular sequence can be performed by methods known to those skilled in the art. One such method is the enzymatic nucleic acid amplification from the U3' bearing VL30 sequence using polymerase chain reaction, wherein the amplified product is purified using standard biochemical techniques and comprises the mammalian anoxia-responsive element. Another method is the use of a nucleic acid synthesizer, and the related standard biochemical techniques, in which the mammalian anoxia-responsive element can be chemically synthesized.

In summary of one mode of this embodiment, a process for making a mammalian anoxia-responsive element comprises the steps of isolating a U3' bearing VL30 sequence; insertion of the U'3 bearing VL30 sequence into a reporter vector so as to be operably linked to a reporter gene in the reporter vector in forming a recombinant reporter construct; introduction of the recombinant reporter construct into mammalian cells capable of undergoing an anoxic response; culturing a portion of the mammalian cells containing the recombinant reporter construct in anoxic conditions, and a portion in aerobic conditions; assaying the anoxia-exposed cells and the aerobically grown cells for expression of the reporter gene, wherein induction of expression of the reporter gene in anoxia-exposed cells relative to the level of expression of the reporter gene in aerobically grown cells indicates that the sequence comprises a mammalian anoxia-responsive element.

A modification of this mode of the embodiment is to reduce the size of the mammalian anoxia-responsive element made accordingly to the process of the invention as recited above. This modification further includes the steps of creating deletions of the VL30 sequence in partial sequences; inserting the partial sequences into a reporter vector so as to be operably linked to a reporter gene in the reporter vector in forming a recombinant reporter construct; introduction of the recombinant reporter construct into mammalian cells capable of undergoing an anoxic response; culturing a portion of the mammalian cells containing the recombinant reporter construct in anoxic conditions, and a portion in aerobic conditions; assaying the anoxia-exposed cells and the aerobically grown cells for expression of the reporter gene, wherein induction of expression of the reporter gene in anoxia-exposed cells relative to the level of expression of the reporter gene in aerobically grown cells indicates that the partial sequence comprises a mammalian anoxic-responsive element.

Another variation of this embodiment is directed to a process of making a mammalian anoxia-responsive element of a particular known sequence. A process of making a mammalian anoxic-responsive element of a particular known sequence comprises a method selected from the group consisting of enzymatic nucleic acid amplification from a U3' bearing VL30 sequence wherein the amplified product is purified using standard biochemical techniques and comprises the mammalian anoxia-responsive element, and chemically synthesizing the mammalian anoxia-responsive element.

EXAMPLE 2

Methods for modifying a mammalian anoxia-responsive element

Using the illustrative methods and constructs according to Example 1, a mammalian anoxia-responsive element can be produced from cellular or retroviral DNA. It is apparent to those skilled in the art that a mammalian anoxia-responsive element, that is the functional equivalent of the mammalian anoxia-responsive element produced in accordance with the methods of Example 1, may be produced by modifying the nucleotide sequence of the mammalian anoxia-responsive element produced in accordance with the methods of Example 1. One method of modification involves mutation of the nucleotide sequence of the mammalian anoxia-responsive element.

To illustrate this embodiment, a series of oligonucleotides (SEQ ID NOs: 2–14) were synthesized which contained random point mutations spanning the nucleotide sequence, SEQ ID NO:1 (Estes et al. 1995, supra). The oligonucleotides also contained a sequence comprising a tail which could be promoted to self anneal onto itself. Then, these oligonucleotides were made fully double stranded by a primer extension reaction containing deoxynucleoside triphosphates, and Klenow polymerase. The double stranded sequences containing the random point mutations were then cloned into a CAT reporter vector, and assayed for anoxia inducibility using the methods described in Example 1. The effect of the various point mutations on the anoxic inducibility of SEQ ID NO:1 is illustrated in FIG. 3. Relative CAT activity for each mutant in anoxic culture is compared to the relative CAT activity for each mutant in aerobic culture. It is noted that most mutations (SEQ ID NOs: 2,3,5–10, 13 and 14) demonstrated a significant reduction (>50% reduction) in the ability of the respective mutant to enhance CAT activity after anoxia, as compared to the unmodified sequence. Two mutants (SEQ ID Nos: 11 and 12) showed substantial reduction (≦50% reduction) in the ability to enhance CAT activity after anoxia. Particularly interesting is one mutant (SEQ ID NO:4), differing in one base change from SEQ ID NO:1, which showed an slightly increased ability to enhance CAT activity after anoxia as compared to SEQ ID NO:1. Thus, a mammalian anoxia-responsive element may be modified by synthesizing a sequence differing by a limited number of base changes or substitutions, wherein the modified sequence is a functional equivalent of the original sequence in that the modified sequence has the ability to substantially induce expression of a desired DNA molecule in the cells under anoxic conditions, as compared to the level of induction demonstrated by the unmodified mammalian anoxia-specific responsive element.

EXAMPLE 3

Further characterization of the mammalian anoxia-responsive element

In characterizing the mammalian anoxia-responsive element represented by SEQ ID NO:1, a comparison of the nucleotide sequence of SEQ ID NO:1 with known sequences contained in a database revealed that SEQ ID NO:1 contained an identity of seven-of-eight nucleotides in the consensus binding site for hypoxia-inducible factor 1 (HIF-1; Semenza et al., 1994, J. Biol. Chem. 269:23757–23763). The modification of SEQ ID NO:1 by creating deletion mutants showed that mutations outside the region of identity with HIF-1 significantly reduced the ability of the respective mutant to enhance CAT activity after anoxia, as compared to the unmodified sequence. Moreover, a modification which creates a perfect match to the consensus HIF-1 binding site also significantly reduced the ability of the respective mutant to enhance CAT activity after anoxia, as compared to the unmodified sequence. Thus, the mammalian anoxia-responsive element represented by SEQ ID NO:1 is functionally distinct from the consensus HIF-1 binding site.

The functional distinction was further elucidated in characterizations using a reporter construct, and using electrophoretic mobility shift assays (Estes et al., 1995, supra). A recombinant CAT reporter construct containing SEQ ID NO:1 was used in transfections of cultured fibroblasts subsequently grown in aerobic conditions, hypoxic conditions, and anoxic conditions. It was demonstrated, for example, that under hypoxia only a 2.8 fold induction of CAT activity was observed, relative to the level measured from aerobically cultured cells. In contrast, under anoxia, an 8.8 fold induction was observed. Thus, HIF-1 alone is not sufficient for the activity of the mammalian anoxia-responsive element represented by SEQ ID NO:1 observed during anoxia. In fact, electrophoretic mobility shift assays confirmed that a new factor, anoxic-inducible factor (AIF) is required for strongly inducing the mammalian anoxia-responsive element activity in anoxic fibroblasts. It was shown from extracts of anoxic fibroblasts that the abundance of AIF-mammalian anoxia-responsive element complexes compared to HIF-1-mammalian anoxia-responsive element complexes is 10:1. Further, it was shown that AIF is a heterodimer composed of subunits with calculated molecular masses of 61 kilodaltons (kDa) and 52 kDa. In contrast, HIF-1 is a heterodimer composed of subunits of 120 kDa and 94 kDa. Additionally, hypoxic fibroblasts, while sufficient to induce a low level of HIF-1 binding, fail to induce AIF binding to mammalian anoxia-responsive element represented by SEQ ID NO1:. Thus, it has been demonstrated that the strong induction of expression of a DNA molecule operably linked to a mammalian anoxia-responsive element observed in anoxic cells occurs through a mechanism specific to anoxia.

EXAMPLE 4

Method for inducing the expression of a DNA molecule under regulatory control of a mammalian anoxia-responsive element This example describes cloning, transformation, and expression techniques and considerations for inducing the expression of a DNA molecule under the regulatory control of a mammalian anoxia-responsive element in mammalian cells capable of undergoing an anoxic response, whether the cells are cultured in vitro, or are cells present in vivo. A mammalian anoxia-responsive element according to the present invention is useful for regulating the expression of a DNA molecule which is operably linked to a promoter and a mammalian anoxia-responsive element ("DNA-promoter-MARE construct") upon introducing the DNA-promoter-MARE construct into mammalian cells capable of undergoing an anoxic response and which are then exposed to anoxia. Alternatively, the DNA-promoter-MARE construct is incorporated into a vector capable of replication and expression in a mammalian cell (in forming a "recombinant vector"), and the recombinant vector is introduced into mammalian cells capable of undergoing an anoxic response, with subsequent exposure of those cells to anoxic conditions.

The DNA-promoter-MARE construct, and the recombinant vector, can be used to place the expression of a desired DNA molecule under regulation by anoxic induction. As defined, the DNA-promoter-MARE construct comprises a DNA molecule operably linked to a promoter and to a mammalian anoxia-responsive element. As understood by one skilled in the art, the combination of the DNA molecule with a promoter and a mammalian anoxia responsive element into a construct must be made in a proper orientation and reading frame such that the DNA molecule to be expressed is transcribed into functional RNA with the transcription being regulated by the mammalian anoxia-responsive element and promoter. A mammalian anoxia-responsive element according to the present invention is a cis-acting regulatory element. As a cis-acting element, a mammalian anoxia-responsive element may be placed as an "upstream enhancer" located 5' to the promoter-DNA molecule combination, as a "promoter element" located as part of the promoter complex or between the promoter and the DNA molecule to be expressed, or as a "downstream enhancer" located within the first third of the coding region of the DNA molecule to be expressed. For example, the mammalian anoxia-responsive element appears in VL30 LTR as part of the promoter complex comprising the LTR, and thus appears as a promoter element. As illustrated in Example 1 in producing the deletion constructs, the sequence containing a mammalian anoxia-responsive element was inserted downstream from a basal SV40 promoter but upstream from the reporter gene, and thus appears as a promoter element. However, a sequence identical to SEQ ID NO:1 has been found within a gene of the major histocompatibility complex (MHC), thus appearing as a downstream enhancer, with the degree of anoxic inducibility presently being further characterized. Enhancers, inducible by physiologic agents or conditions other than anoxia, have been identified in VL30 sequences and can regulate transcription as "upstream enhancers" (retinoic acid inducible- Islam et al., 1993, *J. Biol. Chem.* 268:3251-3259; 12-O-tetradecanoylphorbol-13-acetate inducible-Bohm, 1991, *J. Biol. Chem.* 266:24834-24841). Like other cis-acting VL30 enhancers, a mammalian anoxia-responsive element may be placed as an upstream enhancer located 5' to the promoter-DNA molecule combination. Placement of an mammalian anoxia-responsive element either upstream or downstream from the promoter to induce transcription subsequent to initiation of anoxia is also dependent on the mammalian cell-type and expression vector system used.

The DNA-promoter-MARE construct by itself, or incorporated into a vector in forming a recombinant vector, is introduced into mammalian cells capable of undergoing an anoxic response. The method of introducing DNA comprising DNA-promoter-MARE construct or the recombinant vector into a mammalian cell can depend on whether the cell is in vitro or in vivo. In one variation, the DNA can be applied to the cell or cell environment directly ("direct DNA transfer") in vivo. For example, direct transfer of DNA into a individual, resulting in expression of the DNA by the individual's cells such as vascular endothelial cells as well as the tissue of the major organs, has been demonstrated by techniques in the art such as by injecting intravenously an expression plasmid:cationic liposome complex (Zhu et al., 1993, *Science* 261:209–211). Another liposome formulation with either encapsulated sense DNA or antisense DNA was selectively endocytosed by both lymphocytes and monocytes (Sullivan et al., 1992, *Antisense Res. Dev.* 2:3 187–197). Other effective methods for delivering DNA into a target cell in vivo are known in the art. In one example, purified recombinant plasmid DNA containing viral genes has been used to introduce (whether parentally, mucosally, or via gene-gun) into an individual a gene that is then expressed into a gene product (Fynan et al., 1993, *Proc. Natl. Acad. Sci. USA* 90:11478–11482).

In another example, cells removed from an individual can be transfected or electroporated by standard procedures known in the art, resulting in the introduction of the recombinant vector into the target cell. Cells containing the recombinant vector may then be selected for using methods known in the art such as via a selection marker expressed in the vector, and the selected cells may then be re-introduced into the individual to express the DNA molecule. In this embodiment, the DNA can be administered in a pharmaceutically acceptable carrier or diluent which may increase the uptake of nucleic acid by the cells. Likewise, the same introduction and screening techniques may be used to introduce recombinant vector into mammalian cells in vitro. Cells upon which resistance to infection is to be conferred, are transformed with a polynucleotide via a vector. There are many methods of introducing a recombinant vector into a mammalian cell including, but not limited to, transformation, transfection, microinjection, $CaPO_4$ precipitation, electroporation, targeted liposomes, particle-gun bombardment, electrofusion, and infection. Selectable markers for detection and isolation of cells successfully having introduced into them a recombinant vector containing the marker, include without limitation antibiotic resistance to neomycin, ampicillin, or xanthine.

Vectors, used in accordance with the present invention as a vehicle for introducing into a mammalian cell and expressing the DNA-promoter-MARE construct incorporated therein, can be selected from plasmids, viruses, and retroviruses. The features of a vector which make it useful in the methods of the present invention include that it have a selection marker for identifying mammalian cells which have been transfected by the vector in vitro; and restriction sites to facilitate cloning of a DNA-promoter-MARE construct as an insert in forming the recombinant vector. Examples of useful vectors for the in vitro or in vivo introduction of a recombinant vector into mammalian cells include, but are not limited to retroviral vectors. A retroviral vector, such as a plasmid containing AAV (Adeno-associated virus) sequences, has been described previously (see for example Chatterjee et al., 1992, *Science*, 258:1485–1488). A preferred AAV vector contains inverted terminal repeats (ITR) with a selection marker such as the gene encoding neomycin resistance, an SV40 promoter, a polylinker, and other plasmid sequences. A promoter in the ITR drives the expression of the neomycin phosphotransferase gene, whereas the SV40 promoter drives expression of the operably linked DNA molecule to be expressed. The mammalian anoxia-responsive element is placed, relative to the promoter and DNA molecule, as an upstream enhancer, as a promoter element, or as a downstream enhancer. The inverted terminal repeats of the AAV vector provide a means for integrating the vector, and sequences inserted therein, into the chromosome as the repeats serve as a sequence which has been shown to insert site-specifically, rather than randomly, into chromosomes.

Examples of other vectors for the in vitro or in vivo introduction of a recombinant vector into mammalian cells include retroviral vectors disclosed by Miller et al. (1989, *BioTechniques* 7:980–990), and adenovirus vectors. In a preferred embodiment, and particularly relevant to the expression of a DNA molecule regulated by induction of a mammalian anoxia-responsive element comprising a nucleic acid sequence derived from VL30 sequences, novel vectors are made from mouse VL30 retrotransposons (Chakraborty et al., 1995, *Biochem. Biophys. Res. Commun.* 209:677–683). Such vectors have been tested in human cell types including skeletal muscle epithelium, bronchial epithelium, mammary epithelium, immortalized peripheral blood lymphocytes, and various tumor cell lines. The VL30 vectors were expressed as abundant mRNAs in all human cells tested and can be regulated by an inducible regulatory element in a cell type-specific fashion (Chakraborty et al., 1995, supra). The mammalian anoxia-responsive element is placed, relative to the promoter and DNA molecule in forming a recombinant VL30 vector, as an upstream enhancer, as a promoter element, or as a downstream enhancer.

Another VL30 vector has been recently described which comprises a murine leukemia virus (MLV)-VL30-derived vector for gene transfer (Torrent et al., 1994, *J. Virol.* 68:661–667). Recombinant MLV-derived vectors are used to introduce homologous and heterologous genes into humans (Dhawan et al., 1991, *Science* 254:1509–1512; Ferry et al., 1991, *Proc. Natl. Acad. Sci. USA* 88:8377–8381). The MLV-VL30-derived vector contains rat VL30 RNA sequence which leads to more efficient packaging, than the replaced sequences, into MoMLV virions and further lacks gag sequences thereby making it unlikely that replication-competent viruses could form via recombination with RNA of the helper cell. Utilization of such a vector is believed to improve the biological safety of gene transfer using recombinant MLV-derived viruses. The mammalian anoxia-responsive element may be placed, relative to the promoter and DNA molecule in forming a recombinant MLV-VL30-derived vector, as an upstream enhancer, as a promoter element, or as a downstream enhancer.

There are several applications for providing a method for regulating the expression of a DNA molecule under anoxic conditions. As illustrated in Example 1, a DNA molecule to be expressed can be regulated by operably linking the DNA molecule to a mammalian-expressible promoter and mammalian anoxia-responsive element in a vector in a cis-acting orientation in forming a recombinant vector; introducing the recombinant vector into a host mammalian cell expression compatible with the mammalian-expressible promoter and mammalian anoxia-responsive element; wherein expression of the DNA molecule is facilitated by exposing the host mammalian cell containing the recombinant vector to anoxic conditions. In response to anoxic conditions, transcription in the cell of an operably-linked promoter-DNA molecule combination is enhanced by the mammalian anoxia-responsive element.

The DNA molecule having its expression regulated by an operably linked mammalian anoxia-responsive element may be a nucleic acid sequence selected from the group consisting of a gene which encodes a desired gene product comprising a protein, more than one gene, a gene fragment comprising a portion of a gene which encodes a desired peptide, and antisense to a gene. The expressed proteins or peptides may include biologically-active, and/or commercially valuable molecules known to those skilled in the art which are produced or desired to be produced in physiological conditions such as wound healing, or a pathological condition such as malignancy, in which cells are exposed to anoxia.

In one embodiment, the mammalian anoxia-responsive element is used to drive the expression of proteins such as cathepsins D and L or endonuclease-NX. These enzymes are useful for debridement in the wound healing process (Stoler et al., 1992, supra). In one variation of this embodiment, these enzymes can be produced in a culture of anoxic fibroblasts. The enzymes can be purified from the culture using methods known to those skilled in the art such as detergent extraction, chromatographic techniques, or affinity purification. The enzymes can then be incorporated as an additive to topical preparations to be applied during the wound healing process to facilitate debridement. It is possible to cycle the culture between anaerobic and aerobic conditions in order to obtain cycles of expression and nonexpression (or basal expression) of a DNA molecule operably linked to the mammalian anoxia-responsive element.

In chronic wound situations such as decubitus ulcers (bed sores), wound healing does not progress beyond he debridement stage. Excessive protease action produces ongoing damage to surrounding healthy tissue leading to wound expansion and hence, a non-healing wound (Bennett et al., 1993, *Am. J. Surg.* 166:74; Mawson et al., 1993, *Prev. Med.* 22:433–450). Even though such wounds are on the surface, local tissue oxygen tensions remain anoxic or near anoxic (Remensnyder et al., 1968, *Am. J. Pathol.* 52:301–323) providing an environment wherein a mammalian anoxia-responsive element can be used to drive expression of a desired DNA molecule. One such DNA molecule that may be expressed is a gene encoding transforming growth factor β (TGFβ). TGFβ is a protein that augments the wound healing progression by terminating the debridement phase and promoting progression to the proliferative phase including collagen production, neovascularization, and cell proliferation (Bennett et al., 1993, *Am. J. Surgery* 165:728–737). In small non-healing wounds, TGFβ as produced and purified from anoxic cells cultured in vitro, can be applied to the wound site to augment wound healing progression. In larger non-healing wounds, periodic application of TGFβ would likely lead to degradation of the factor by the large highly proteolytic environment. Thus, a means of continual production of TGFβ until wound healing progresses beyond an anoxic environment may be achieved by introducing a recombinant vector with the gene encoding TGFβ operably linked to a mammalian anoxia-responsive element to drive production of TGFβ and thus, progression beyond the debridement stage. Methods known to those skilled in the art, as described in more detail above, can be used for introducing such a recombinant vector into cells at the non-healing wound site.

In another embodiment, the mammalian anoxia-responsive element is used to drive the expression of a desired DNA molecule for gene therapy in cancer treatment. A review of clinical applications of gene therapy for cancer is provided by Culver (1994, *Clin. Chem.* 40:510–512). As described previously, malignant tumor seeds and proliferates in an anoxic environment either prior to revascularization which then restores aerobic conditions, or where proliferation has outgrown vascularization (See also, Kinzler et al., 1996, *Nature* 379:19–20). Malignant tumors express key features of the anoxic fibroblast response observed in wound healing. Proteases cathepsins D and L, endonuclease-NX, and LDH-κ activity are associated with malignancy. A critical difference between a malignant tumor and a benign tumor is the ability of the malignant tumor, via expression of the proteases, to break down intercellular matrices and adhesions in surrounding tissues, permitting tumor cell invasion (Anderson et al., 1993, supra). Further, endonuclease-NX contributes to the genomic instability of a malignant tumor and subsequent properties of metastasis and drug resistance (Russo et al., 1995, *Cancer Res.* 55:1122–1128). Thus, approaches to antitumor therapy, particularly in an anoxic environment prior to revascularization of a tumor or as a result of outgrowth from vascularization, may be achieved by introducing into such tumor cells a recombinant vector with a DNA molecule encoding antisense to one or more of the genes encoding proteases cathepsins D and L, endonuclease-NX, and LDH-κ activity operably linked to a mammalian anoxia-responsive element to drive production of the antisense in modulating protease expression and its associated tumor cell invasion, and genomic instability. Alternatively, one or more genes may be desired to be expressed as antitumor therapy in the anoxic environment. To prevent angiogenesis of the malignant tumor (thereby cutting off the tumor's blood supply), one or more genes encoding angiogenesis inhibitors may be operably linked to a mammalian anoxia-responsive element. Angiogenesis inhibitors are known to those skilled in the art to include angiostatin and thrombospondin (O'Reilly et al., 1994, Cell 79:315–328). In yet another alternative, a gene encoding a gene product directly or indirectly results in cell death may be operably linked to a mammalian anoxia-responsive element for antitumor therapy in tumor cells in an anoxic environment. In that regard, a gene product that promotes direct cell toxicity, such as diphtheria toxin, or indirect cell toxicity, such as immunostimulatory cytokines (Culver, 1994, supra) is produced. Methods known to those skilled in the art, as described in more detail above, can be used for introducing a recombinant vector containing one or more of such genes for antitumor activity, into tumor cells (See also, Culver, 1994, supra).

From the foregoing, it will be obvious to those skilled in the art that various modifications in the above-described methods, constructs and cells can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the claims are therefore intended to be embraced therein.

We claim:

1. An isolated and purified nucleic acid molecule consisting of mammalian anoxia-responsive element or a functional equivalent thereof, wherein the mammalian anoxia-responsive element consists of the nucleotide sequence disclosed in SEQ ID NO:1 or a nucleotide sequence which is identical to SEQ ID NO:1 except for a one base change or substitution, and wherein the functional equivalent is a VL30-derived sequence of 14 bp.

2. A recombinant DNA molecule comprising:
   (a) the nucleic acid molecule according to claim 1;
   (b) a mammalian-expressible promoter; and
   (c) a DNA molecule to be expressed in a mammalian cell under anoxic conditions;
   wherein the DNA molecule is operably linked to the promoter and the nucleic acid molecule according to claim 1 in a proper orientation and reading frame such that the DNA molecule is transcribed into functional RNA in a mammalian cell with the transcription being enhanced by the nucleic acid molecule according to claim 1 in response to anoxia.

3. The recombinant DNA molecule according to claim 2, wherein said mammalian anoxia-responsive element consists of the nucleotide sequence disclosed in SEQ ID NO:1 or a nucleotide sequence which is identical to SEQ ID NO:1 except for a one base change or substitution.

4. A recombinant vector, which replicates in a mammalian cell, comprising:
   (a) the nucleic acid molecule according to claim 1;
   (b) a mammalian-expressible promoter; and
   (c) a DNA molecule to be expressed in a mammalian cell under anoxic conditions;
   wherein the DNA molecule is operably linked to the promoter and the nucleic acid molecule according to claim 1 in a proper orientation and reading frame such that the DNA molecule is transcribed into functional RNA in a cell with the transcription being enhanced by the nucleic acid molecule according to claim 1 in response to anoxia.

5. The recombinant vector according to claim 4, wherein said nucleic acid molecule is a mammalian anoxia-responsive element consisting of the nucleotide sequence disclosed in SEQ ID NO:1 or a nucleotide sequence which is identical to SEQ ID NO:1 except for a one base change or substitution.

6. The recombinant vector according to claim 4, wherein said vector contains a selectable marker for antibiotic resistance.

7. A cell which contains the recombinant vector of claim 4.

8. A cell which contains the recombinant vector of claim 5.

9. A cell which contains the recombinant vector of claim 6.

10. A process for making a mammalian anoxia-responsive element comprising the steps of:
    (a) isolating a U3' bearing VL30 sequence from cellular or retroviral nucleic acid;
    (b) inserting the U3' bearing VL30 sequence into a reporter vector so as to operably link the VL30 sequence to a reporter gene in a reporter vector in forming a recombinant reporter construct;
    (c) introducing the recombinant reporter construct into mammalian cells which undergoes an anoxic response;
    (d) culturing equal and separate portions of the mammalian cells containing the recombinant reporter construct in anoxic conditions, and in aerobic conditions;
    (e) assaying the anoxic-cultured cells and the aerobically cultured cells for expression of the reporter gene, wherein induction of expression of the reporter gene in anoxic-cultured cells relative to the level of expression of the reporter gene in aerobically cultured cells indicates that the VL30 sequence comprises a mammalian anoxia-responsive element; and
    (f) isolating the mammalian anoxia-responsive element from the recombinant reporter construct.

11. A modification of the process according to claim 10, wherein the VL30 sequence is reduced in size to produce a nucleotide sequence consisting of the mammalian anoxia-responsive element, said modification comprises the additional steps of:
    (a) inserting portions of the VL30 sequence identified from claim 10 step (e) as comprising the mammalian anoxia-responsive element into reporter vectors so as to operably link the portions of the VL30 sequence to a reporter gene in the reporter vectors in forming recombinant reporter constructs;
    (c) introducing each recombinant reporter construct into mammalian cells which undergoes an anoxic response;
    (d) culturing equal and separate portions of the mammalian cells containing each recombinant reporter construct in anoxic conditions, and in aerobic conditions;
    (e) assaying the anoxic-cultured cells and the aerobically cultured cells for expression of the reporter gene, wherein induction of expression of the reporter gene in anoxic-cultured cells relative to the level of expression of the reporter gene in aerobically cultured cells indicates that the portion of the VL30 sequence consists of a mammalian anoxia-responsive element; and
    (f) isolating the mammalian anoxia-responsive element from the recombinant reporter construct.

12. A process of making a mammalian anoxia-responsive element, wherein said process is selected from the group consisting of using enzymatic nucleic acid amplification to amplify the mammalian anoxia-responsive element from a U3' bearing VL30 sequence containing the mammalian anoxia-responsive and subsequently purifying the amplified product comprising the mammalian anoxia-responsive element, and chemically synthesizing the mammalian anoxia-responsive element.

13. A method for regulating the expression of a desired DNA molecule which comprises:
    (a) operably linking said DNA molecule to the nucleic acid molecule according to claim 1 and a mammalian-expressible promoter in a vector and in a proper orientation and reading frame such that the DNA molecule is transcribed into functional RNA in a cell with the transcription being enhanced by the nucleic acid molecule according to claim 1 in response to anoxia;
    (b) introducing said vector into mammalian cells which undergoes an anoxic response; and
    (c) regulating the expression of said desired DNA molecule by exposing the mammalian cells from step (b) to anoxia.

14. The method according to claim 13, wherein said mammalian anoxia-responsive element consists of the nucleotide sequence disclosed in SEQ ID NO:1 or a nucleotide sequence which is identical to SEQ ID NO:1 except for a one base change or substitution.

15. A method for inducing a high level of expression of a desired DNA molecule that is operably linked to a mammalian-expressible promoter and a nucleic acid molecule according to claim 1 wherein the transcription of said DNA molecule is regulated by the nucleic acid molecule according to claim 1, said method comprising introducing into a mammalian cell which undergoes an anoxic response the recombinant vector of claim 4, and subsequently exposing the mammalian cell containing the recombinant vector to anoxia such that expression of the desired DNA molecule is increased over a basal level of expression by the DNA molecule operably linked only to the promoter.

16. The method according to claim 15, wherein said mammalian anoxia-responsive element consists of the nucleotide sequence disclosed in SEQ ID NO:1 or a nucleotide sequence which is identical to SEQ ID NO:1 except for a one base change or substitution.

* * * * *

SEQUENCE LISTING ( 1 ) GENERAL INFORMATION:

( i i i ) NUMBER OF SEQUENCES: 16

( 2 ) INFORMATION FOR SEQ ID NO:1 :

( i ) SEQUENCE CHARACTERISTICS:
        ( A ) LENGTH: 14 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:1 :

TAGCACGTAC TCTT    14

( 2 ) INFORMATION FOR SEQ ID NO:2 :

( i ) SEQUENCE CHARACTERISTICS:
        ( A ) LENGTH: 14 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:2 :

AAGCACGTAC TCTT    14

( 2 ) INFORMATION FOR SEQ ID NO:3 :

( i ) SEQUENCE CHARACTERISTICS:
        ( A ) LENGTH: 14 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:3 :

CAGCACGTAC TCTT                                                                                              14

(2) INFORMATION FOR SEQ ID NO:4 :

(i) SEQUENCE CHARACTERISTICS:
        (A) LENGTH: 14 nucleotides
        (B) TYPE: nucleic acid
        (C) STRANDEDNESS: double-stranded
        (D) TOPOLOGY: linear (ii) MOLECULE TYPE: DNA (iii) HYPOTHETICAL: No (iv) SEQUENCE DESCRIPTION: SEQ ID NO:4 :

TCGCACGTAC TCTT                                                                                              14

(2) INFORMATION FOR SEQ ID NO:5 :

(i) SEQUENCE CHARACTERISTICS:
        (A) LENGTH: 14 nucleotides
        (B) TYPE: nucleic acid
        (C) STRANDEDNESS: double-stranded
        (D) TOPOLOGY: linear (ii) MOLECULE TYPE: DNA (iii) HYPOTHETICAL: No (iv) SEQUENCE DESCRIPTION: SEQ ID NO:5 :

TATCACGTAC TCTT                                                                                              14

(2) INFORMATION FOR SEQ ID NO:6 :

(i) SEQUENCE CHARACTERISTICS:
        (A) LENGTH: 14 nucleotides
        (B) TYPE: nucleic acid
        (C) STRANDEDNESS: double-stranded
        (D) TOPOLOGY: linear (ii) MOLECULE TYPE: DNA (iii) HYPOTHETICAL: No (iv) SEQUENCE DESCRIPTION: SEQ ID NO:6 :

TAGATCGTAC TCTT                                                                                              14

(2) INFORMATION FOR SEQ ID NO:7 :

(i) SEQUENCE CHARACTERISTICS:
        (A) LENGTH: 14 nucleotides
        (B) TYPE: nucleic acid
        (C) STRANDEDNESS: double-stranded
        (D) TOPOLOGY: linear (ii) MOLECULE TYPE: DNA (iii) HYPOTHETICAL: No (iv) SEQUENCE DESCRIPTION: SEQ ID NO:7 :

TAGCAAGTAC TCTT                                                                                              14

(2) INFORMATION FOR SEQ ID NO:8 :

(i) SEQUENCE CHARACTERISTICS:
        (A) LENGTH: 14 nucleotides
        (B) TYPE: nucleic acid
        (C) STRANDEDNESS: double-stranded
        (D) TOPOLOGY: linear (ii) MOLECULE TYPE: DNA (iii) HYPOTHETICAL: No (iv) SEQUENCE DESCRIPTION: SEQ ID NO:8 :

TAGCACTTAC TCTT 14

(2) INFORMATION FOR SEQ ID NO:9 :

(i) SEQUENCE CHARACTERISTICS:
  (A) LENGTH: 14 nucleotides
  (B) TYPE: nucleic acid
  (C) STRANDEDNESS: double-stranded
  (D) TOPOLOGY: linear (ii) MOLECULE TYPE: DNA (iii) HYPOTHETICAL: No (iv) SEQUENCE DESCRIPTION: SEQ ID NO:9 :

TAGCACGGAC TCTT 14

(2) INFORMATION FOR SEQ ID NO:10 :

(i) SEQUENCE CHARACTERISTICS:
  (A) LENGTH: 14 nucleotides
  (B) TYPE: nucleic acid
  (C) STRANDEDNESS: double-stranded
  (D) TOPOLOGY: linear (ii) MOLECULE TYPE: DNA (iii) HYPOTHETICAL: No (iv) SEQUENCE DESCRIPTION: SEQ ID NO:10 :

TAGCACGTCC TCCT 14

(2) INFORMATION FOR SEQ ID NO:11 :

(i) SEQUENCE CHARACTERISTICS:
  (A) LENGTH: 14 nucleotides
  (B) TYPE: nucleic acid
  (C) STRANDEDNESS: double-stranded
  (D) TOPOLOGY: linear (ii) MOLECULE TYPE: DNA (iii) HYPOTHETICAL: No (iv) SEQUENCE DESCRIPTION: SEQ ID NO:11 :

TAGCACGTAA TCTT 14

(2) INFORMATION FOR SEQ ID NO:12 :

(i) SEQUENCE CHARACTERISTICS:
  (A) LENGTH: 14 nucleotides
  (B) TYPE: nucleic acid
  (C) STRANDEDNESS: double-stranded
  (D) TOPOLOGY: linear (ii) MOLECULE TYPE: DNA (iii) HYPOTHETICAL: No (iv) SEQUENCE DESCRIPTION: SEQ ID NO:12 :

TAGCACGTAC ACTT 14

(2) INFORMATION FOR SEQ ID NO:13 :

(i) SEQUENCE CHARACTERISTICS:
  (A) LENGTH: 14 nucleotides ( B ) TYPE: nucleic acid
        ( C ) STRANDEDNESS: double-stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:13:

TAGCACGTAC TTTT  14

( 2 ) INFORMATION FOR SEQ ID NO:14 :

( i ) SEQUENCE CHARACTERISTICS:
        ( A ) LENGTH: 14 nucleotides
        ( B ) TYPE: nucleic acid
        ( C ) STRANDEDNESS: double-stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:14 :

TAGCACGTAC TCTA  14

( 2 ) INFORMATION FOR SEQ ID NO:15 :

( i ) SEQUENCE CHARACTERISTICS:
        ( A ) LENGTH: 424 nucleotides
        ( B ) TYPE: nucleic acid
        ( C ) STRANDEDNESS: single-stranded
        ( D ) TOPOLOGY: unknown ( i i ) MOLECULE TYPE: DNA ( i i i ) HYPOTHETICAL: No ( i v ) SEQUENCE DESCRIPTION: SEQ ID NO:15 :

GGAGAAGACA GGAATGAAAA GAAAATTATA TAAATTCTAG GTTTAAAAAT  50
ATAAAAATTA AAAAAATAAA CCCCAAAAGG CCACAGACCC AGGGCTAAGC  100
CCTGCATGCC AAGACTAGCA GGCCATAAAG ATAAAGGAGC ACAGGAAACA  150
CTGTTCAGGC AGGACTGACA AGCCATAAAA AAAGGAATGC AGGAACCAGC  200
CTGAGTTATG AGACTGATTC ATGGGACGTC TGGCAGGAAG ACAATCTCCC  250
CCCAGCTCAC TCAGGCCATA TTTCAACTAG GTGTCCTCCA GCCCCTGATA  300
AGCCCCTGAC TTCTAGCACG TACTCTTTCT GCTTTGTTCT CACTGCTATG  350
TTTGAATGAG CCAATTGTAT GTAACCACGC CAAAACCCCT AGCCTTCTCT  400
ATATAACCCT CTGACTTTTG AGTT  424

( 2 ) INFORMATION FOR SEQ ID NO:16 :

( i ) SEQUENCE CHARACTERISTICS:
        ( A ) LENGTH: 21 nucleotides
        ( B ) TYPE: nucleic acid
        ( C ) STRANDEDNESS: single-stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:16 :

CTTCTTGGAC TGTGCCTCAG G  21